United States Patent [19]

Trostmann et al.

[11] Patent Number: 5,750,555
[45] Date of Patent: May 12, 1998

[54] BIS-INDOLYL MALEINIMIDE OR INDOLOPYRROLO CARBAZOLE CONTAINING AN AMINO ACID AS PKC INHIBITORS

[75] Inventors: Uwe Trostmann, March-Hugstetten; Christoph Schachtele, Freiburg; Johannes Hartenstein, Stegen-Wittental; Claus Rudolph, Vorstetten; Hubert Barth, Emmendingen; Reinhard Reck, Sexau; Walter Kolch, Munich, all of Germany

[73] Assignee: Goedecke Aktiengesellschaft, Berlin, Germany

[21] Appl. No.: 464,666

[22] PCT Filed: Dec. 20, 1993

[86] PCT No.: PCT/EP93/03611

§ 371 Date: Nov. 15, 1996

§ 102(e) Date: Nov. 15, 1996

[87] PCT Pub. No.: WO94/14798

PCT Pub. Date: Jul. 7, 1994

[30] Foreign Application Priority Data

Dec. 21, 1992 [DE] Germany .................. 42 43 321.5

[51] Int. Cl.⁶ .................. A61K 31/40; C07D 487/14; C07D 487/22
[52] U.S. Cl. .................. 514/410; 548/416
[58] Field of Search .................. 548/416; 514/410

[56] References Cited

U.S. PATENT DOCUMENTS

| | | | |
|---|---|---|---|
| 4,855,489 | 8/1989 | Trostmann et al. | 560/250 |
| 4,912,107 | 3/1990 | Kleinschroth et al. | 514/232.5 |
| 5,043,335 | 8/1991 | Kleinschroth et al. | 514/211 |
| 5,106,864 | 4/1992 | Suda et al. | 514/410 |
| 5,185,352 | 2/1993 | Aranda et al. | 514/348 |
| 5,322,844 | 6/1994 | Aranda et al. | 514/235.5 |
| 5,380,746 | 1/1995 | Barth et al. | 514/414 |
| 5,401,875 | 3/1995 | Trostmann et al. | 562/567 |
| 5,438,050 | 8/1995 | Kleinschroth et al. | 514/183 |
| 5,461,146 | 10/1995 | Lewis et al. | 540/545 |
| 5,468,872 | 11/1995 | Glicksman et al. | 548/416 |
| 5,475,110 | 12/1995 | Hudkins et al. | 546/256 |
| 5,489,608 | 2/1996 | Kleinschroth et al. | 514/410 |
| 5,516,771 | 5/1996 | Dionne et al. | 514/211 |
| 5,547,976 | 8/1996 | Slater et al. | 514/410 |
| 5,618,809 | 4/1997 | Barrabee et al. | 514/211 |

FOREIGN PATENT DOCUMENTS

| | | | |
|---|---|---|---|
| 14-187686 | 7/1992 | Japan | 548/416 |
| 93/24491 | 12/1993 | WIPO | 548/416 |

*Primary Examiner*—Floyd D. Higel
*Attorney, Agent, or Firm*—Elizabeth M. Anderson

[57] ABSTRACT

The instant invention is a compound of formula

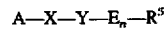

$$A-X-Y-E_n-R^5$$

in which A is a bis-indolylmaleinimide or indolopyrrolocarbazole useful in the treatment and/or prevention of cancer, viral diseases, thrombosis, heart rhythm disturbances, atherosclerosis, bronchopulmonary diseases, degenerative diseases of the central nervous system, inflammatory diseases, diseases of the immune system, psoriasis, and immune suppression. A pharmaceutical composition and methods of preparing the compounds are also included.

17 Claims, No Drawings

BIS-INDOLYL MALEINIMIDE OR INDOLOPYRROLO CARBAZOLE CONTAINING AN AMINO ACID AS PKC INHIBITORS

This application is a 317 of PCT/EP93/03611, filed Dec. 20,1993

BACKGROUND

Protein kinase C plays an important key role for intracellular signal transduction and is closely connected with the regulation of contractile, secretory, and proliferative processes. On the basis of these properties, the compounds according to the present invention can be used for the treatment and/or prevention of cancer, viral diseases (for example HIV infections), heart and blood vessel diseases, for example blood pressure, thromboses, heart rhythm disturbances, atherosclerosis, broncho-pulmonary diseases, degenerative diseases of the central nervous system, for example Alzheimer's disease, inflammatory diseases, such as rheumatism and arthritis, diseases of the immune system, such as allergies, as well as psoriasis. Furthermore, the compounds can be used as immune suppressives.

From the literature, synthetic derivatives and compounds which are derived from substructures of the staurosporin aglycone are known as potent inhibitors of protein kinase C (see *J. Med. Chem.*, 35, 177 (1992) ; *J. Med. Chem.*, 35, 994(1992)). The activity mechanism thereof depends upon the displacement of ATP from the catalytic subunit of protein kinase C.

The compounds of Formula I below of the present invention, have been found to be a new group of PKC inhibitors. They contain an amino acid portion which, on the one hand, is derived from a highly-affinity substrate of PKC, represented by the amino acid serine, and on the other hand from an inhibitor, represented by the amino acid alanine (see *Science*, 238, 1726 (1987) ; *Cell. Signalling*, 2, 187 (1990)). Surprisingly, these new compounds of Formula I prove to be not only highly potent but also, as is shown in some of the examples, selective inhibitors of protein kinase C. The action thereof on myosin light chain kinase proves to be considerably weaker.

SUMMARY OF THE INVENTION

The instant invention concerns new amino acid derivatives of formula

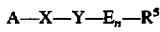

wherein A is

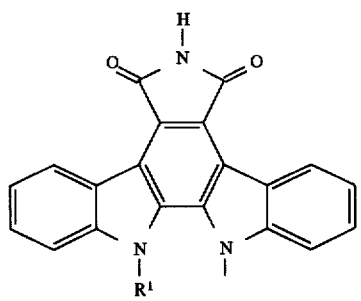

(III)

and X, Y, E, n, and $R^5$ are as described below.

The compounds are potent inhibitors of PKC as can be used in the treatment and/or prevention of cancer, viral diseases including HIV infection, heart and blood vessel diseases, i.e., blood pressure, thrombosis, heart rhythm disturbances, atherosclerosis, broncho-pulmonary, degenerative diseases of the central nervous system, i.e., Alzheimer's disease, inflammatory diseases, i.e., rheumatism and arthritis, diseases of the immune system such as allergies, as well as psoriasis. The compounds can also be used as immune suppressives.

DETAILED DESCRIPTION

The present invention is a new amino acid derivatives of the formula

or a pharmaceutically acceptable salt thereof wherein A is formula

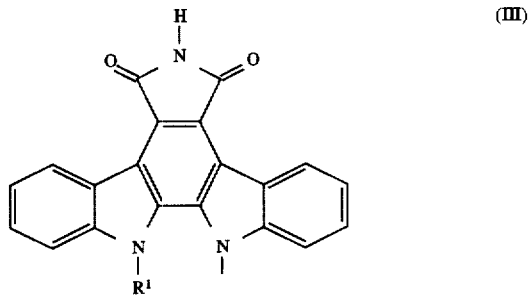

(III)

wherein $R^1$ is hydrogen or alkyl of from 1 to 4 carbon atoms and (———) is open or a valency bond;

X is a single bond or an alkylene radical of from 1 to 16 carbon atoms;

Y is a single bond, N—$R^2$, CO, CS, CH=CH, PO(OH)O, or $SO_2$, wherein $R^2$ is hydrogen or alkyl of from 1 to 4 carbon atoms;

n is an integer of from 1 to 20;

E is the same or different radicals of formula

(IV)

or formula

(V)

wherein $R^2$ is as above and when m is 1, $R^3$ is hydrogen or the side group of a natural α-amino acid and, when m is from 2 to 6, $R^3$ is hydrogen; and $R^5$ is an amino group or —$OR^4$ wherein $R^4$ is alkyl of from 1 to 4 carbon atoms or hydrogen when E is Formula IV and $R^5$ is hydrogen when E is Formula V.

Compounds of Formula I are preferred in which A is a bis-indolylmaleinimide or indolopyrrolocarbazole of Formula III, in which $R^1$ is hydrogen or an alkyl of from 1 to 4 carbon atoms, X is alkylene of from 1 to 10 carbon atoms, Y is NH or CO, E is an aminocarboxylic acid of Formula IV or of Formula V, in which $R^2$ is a hydrogen atom, when m is 1 then $R^3$ is a hydrogen atom or the side group of one of the natural α-amino acids and when m is 1 to 6 then $R^3$ is hydrogen and n is preferably from 1 to 6. The terminal carboxylic acids present in the Formula IV can also be amidated with ammonia or can be esterified with a lower alcohol, for example methanol, ethanol, or propanol.

Furthermore, compounds of Formula I are preferred in which A is bis-indolylmaleinimide or indolopyrrolocarbazole of Formula III in which $R^1$ is methyl, X is methylene, propylene, butylene, pentylene, octylene, or nonylene, Y is either NH or CO, —$E_n$—$R^5$ is alanine, alanine methyl ester, β-alanine, arginine, serine, glycylalanine, glycylglycylalanine, glycylglycylglycylalanine, glycylglycylserine, lysylglycylalanine, serylglycylalanine, alanylglycyllysine, lysylasparaginylarginylphenylalanylalanine, β-alanylalanine, 4-aminovalerianoylserine, or alanylarginine.

Pharmacologically compatible salts of acidic compounds of Formula I with bases and of basic compounds of Formula I with acids, processes for the preparation of compounds of Formula I, pharmaceutical compositions containing compounds of Formula I, and methods of using compounds of Formula I are included in the instant invention.

Compounds of Formula I, in which A, X, Y, and E have the above meanings and n is 1 are prepared either by reacting a compound of the Formula VI $$A-X-Y-G \qquad (VI)$$

in which A and X have the above meanings and —Y—G is an amino group, with an aminocarboxylic acid of the Formula VII

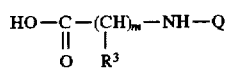  (VII)

in which $R^3$ has the above meaning and functional groups have protective groups and Q is an amino protective group, for example a tert-butoxycarbonyl, benzyloxy-carbonyl or fluorenylmethoxycarbonyl radical, and subsequently splitting off the protective groups according to known processes (for the purpose of the reaction, it is advisable to convert the carboxylic acid group of compounds of Formula VII with the help of dicyclohexylcarbodiimide, pentafluorophenol, or hydroxysuccinimide into activated carboxylic acid esters) or by reacting a compound of Formula VI, in which A and X have the above meanings, Y is CO, CS, CH=CH, PO(OH)O, or $SO_2$ and G is a hydroxyl group or a halogen atom, with an aminocarboxylic acid of the Formula VIII

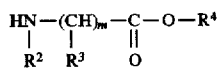  (VIII)

in which $R^2$ and $R^3$ have the above meanings and $R^4$ is methyl, ethyl, or propyl to prepare a compound of formula

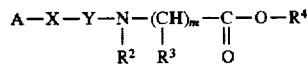  (IX)

in which $R^2$, $R^3$, and $R^4$ have the above meanings. If the compound of Formula VI is present as carboxylic acid, for the purpose of the reaction with a compound of Formula VIII, the carboxylic acid is converted under the usual conditions into an activated ester, for example a pentafluorophenyl ester or a hydroxysuccin-imidyl ester. Compounds of Formula IX are subsequently converted by alkaline saponification of the ester group into compounds of Formula I.

Compounds of Formula I, in which A, X, and Y have the above meanings, which is greater than E is n is greater than 1 a peptide group, are prepared either by reacting a compound of Formula I according to known processes with further aminocarboxylic acids or the synthesis of compounds of Formula I is carried out on solid phases according to the Merrifield method. For this purpose, the first amino acid Formula XI

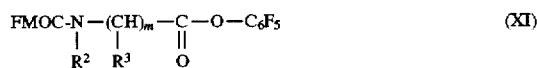  (XI)

in which $R^2$ and $R^3$ have the above meanings, is condensed on to the Merrifield resin. Subsequently the fluorophenylmethoxycarbonyl protective group is split off according to known processes and subsequently, according to requirements, further aminocarboxylic acids of Formula XI are condensed on. In the last condensation step, compounds of Formula VI, in which A and X have the above meanings, Y is CO or CS and G is a hydroxyl group, are reacted in the presence of carboxylic acid-activating compounds, for example dicyclohexylcarbodiimide, with the peptide bound to the Merrifield resin. The splitting off of the compounds of Formula I from the resin takes place according to known processes, for example in trifluoroacetic acid in the presence of phenol. If the synthesis has taken place according to the usual processes, then the end products of Formula I are present as carboxylic acid amides of the Formula Ia $$A-X-Y-E_n-NH_2 \qquad (Ia)$$

If the syntheses are carried out on Wang resin, then the compounds of Formula I are isolated as carboxylic acids.

Compounds of Formula IV, in which A and X have the above meanings and Y is $NH_2$ or COOH, are known. The preparation thereof has been described in the Patent Applications EP 0328026, EP 0384349, EP 0397060 and DE 4217964.5 and in *Tetrahedron Lett.*, 31, 2353 (1,990); *Tetrahedron Lett.*, 31, 5201 (1990) and in the literature cited therein.

The reaction of compounds of Formula VI, in which A and X have the above meanings, Y is N—$R^2$ and G is hydrogen, with aminocarboxylic acids of Formula VII is carried out by placing an aminocarboxylic acid of Formula VII in an aprotic solvent, for example ethyl acetate, dichloromethane, or dimethyl sulphoxide but preferably in dimethylformamide, and converting it with pentafluorophenol or N-hydroxysuccinimide or preferably with dicyclohexylcarbodiimide and in the presence of hydroxybenztriazole into an active carboxylic acid ester and thereafter reacting in the same solvent with a compound of Formula VI at a temperature of from 0° C. to 60° C. but preferably at ambient temperature. The reaction product is purified and isolated according to known processes but preferably chromatographically.

The splitting off of the protective groups is also carried out by generally known processes. The splitting off of the preferred tert-butoxycarbonyl protective group takes place with a strong acid, for example hydrochloric acid but preferably with trifluoroacetic acid, in dichloromethane as solvent at a temperature of from 0° C. to 35° C. but preferably at ambient temperature. After neutralization of the reaction solution, the product is isolated in pure form by precipitation from an appropriate solvent.

Furthermore, compounds of Formula I, in which A and X have the above meanings and E has a terminal carboxylic acid group, are prepared by converting a compound of Formula VI, in which A and X have the above meanings, Y is either CO or CS and G is a hydroxyl group, in an appropriate solvent, preferably dimethylformamide, with pentafluorophenol or N-hydroxysuccinimide and preferably with dicyclohexylcarbodiimide and in the presence of hydroxybenztriazole into an active carboxylic acid ester and thereafter reacted in the same solvent with a compound of the Formula VIII at a temperature of from 0° C. to 60° C. but preferably at ambient temperature. The isolation of the products of Formula IX takes place by conventional processes but preferably with the use of chromatography. The saponification of the carboxylic acid esters of Formula IX to give the desired compounds of Formula I can take place either under acidic or basic conditions, preferably in the presence of alkali metal hydroxides in aqueous organic solvent mixtures but preferably with lithium hydroxide in water/dioxane at a temperature of from 0° C. to 40° C. but preferably at ambient temperature. The products of Formula I are isolated by chromatography and/or crystallization.

Compounds of Formula I, in which A and X have the above meanings, Y is a carbonyl group and E for n>1 is a peptide group, are prepared by condensing an aminocarboxylic acid of Formula XI, in which $R^2$ and $R^3$ have the above meanings, in an aprotic solvent, for example dimethylformamide but preferably DMA, in the presence of hydroxybenztriazole on to a Merrifield resin, washing off excess reagents with the solvent in question, splitting off the fluorenylmethoxycarbonyl protective group under basic conditions, again washing out residual reagents and, in known manner, condensing on further amino acids and, as final partial compound, a compound of Formula VI, in which A and X have the above meanings, Y is CO and G is a hydroxyl group, is condensed on in the same manner. This compound is isolated by treating the Merrifield resin with a strong acid, preferably in the presence of trifluoroacetic acid and of phenol and possibly of thiophenol and thioanisole over the course of several hours and preferably for more than 20 hours at ambient temperature, the resulting dark red solution is separated off and the product, after removal of the solvent, is isolated from diethyl ether in solid form. The product is obtained in pure form chromatographi-cally on RP phase and/or by crystallization.

Compounds of Formula I which have a chiral center can be used as stereoisomeric mixtures or in the form of the enantiomers.

For the purpose of purification and for galenical reasons, basic compounds of Formula I are preferably converted into crystalline, pharmacologically compatible salts. The salts are obtained in the usual way by neutralization of the bases with appropriate inorganic or organic acids. As acids, there can be used, for example, hydrochloric acid, sulphuric acid, phosphoric acid, hydrobromic acid, acetic acid, tartaric acid, lactic acid, citric acid, malic acid, salicylic acid, ascorbic acid, malonic acid, fumaric acid, oxalic acid, or succinic acid. As a rule, the acid-addition salts are obtained in known manner by mixing the free base or a solution thereof with the appropriate acid or a solution thereof in an organic solvent, for example, a lower alcohol, such as methanol, ethanol, or propan-2-ol, or a lower ketone, such as acetone, or butan-2-one, or an ether, such as diethyl ether, diisopropyl ether, tetrahydrofuran, or dioxane.

Compounds of Formula I are potent inhibitors of protein kinase C (PKC).

The compounds can be administered in the particular appropriate formulation enterally or parenterally in dosages of from 1 to 500 mg/kg and preferably of from 1 to 50 mg/kg.

The compounds according to the present invention of Formula I can be administered orally or parenterally in liquid or solid form. As injection medium, there is especially used water which contains the additives usual in the case of injection solutions, such as stabilizing agents, solubilizing agents, or buffers. Such additives include, for example, tartrate and citrate buffers, ethanol, complex formers (such as ethylenediamine-tetraacetic acid and the nontoxic salts thereof), as well as high molecular weight polymers (such as liquid polyethylene oxide) for viscosity regulation. Solid carrier materials include, for example, starch, lactose, mannitol, methyl cellulose, talc, highly dispersed silicic acids, high molecular weight fatty acids (such as stearic acid), gelatine, agar-agar, calcium phosphate, magnesium stearate, animal, and vegetable fats and solid high molecular weight polymers (such as polyethylene glycol). Compositions suitable for oral administration can, if desired, additionally contain flavoring and/or sweetening agents.

The following comparative experiments demonstrate the inhibitory action of the compounds of Formula I of the present invention on protein kinase C.

The enzyme protein kinase C (PKC) is purified from rat brain. Its activity is determined by way of the incorporation of phosphorus $^{32}$-labelled phosphate into a synthetic peptide which is derived from the PKC "pseudosubstrate" sequence (amino acids 19 to 31 of the PKC sequence with alanine in position 25 substituted by serine). A reaction batch of 200 μL contains the following components: 50 mM Tris HCl, pH 7.5, 5 mM $MgCl_2$, 1 mM DTT, 4 μM free $Ca^{2+}$, 10 μM ATP, 1 μg phosphatidylserine, 0.2 μg 1,2-diolein, as well as 0.3 μg peptide substrate. The batch is preincubated for 4 minutes at 30° C. and the reaction then started by the addition of 5 nm PKC. After incubation for 5 minutes at 30° C., the reaction is stopped with 0.73% $H_3PO_4$, and the sample then filtered over a nitrocellulose filter (0.1 μm pore size). The phosphate incorporation is determined by means of Cerenkov counting in a scintillation counter.

The following Table 1 shows the results from this test for a selection of examples. The selectivity of these compounds with regard to other kinases, such as myosin light chain kinase, was tested on the basis of some examples. These values are set out in the following Table 2.

TABLE 1

| Enzyme Test PKC With Peptide Substrate [Ser$^{25}$] PKC (19–31) | |
|---|---|
| Example | Inhibition $IC_{50}$ (nM) |
| 1 | 14 |
| 1a | 6.3 |
| 1b | 23 |
| 2 | 28 |
| 2a | 25 |
| 2b | 220 |
| 2c | >100 |
| 2d | >1000 |
| 2e | >1000 |
| 2f | 330 |
| 3 | 61 |
| 4 | 36 |
| 4a | 18 |
| 5 | 580 |
| 7 | 230 |
| 7a | >100 |
| 7b | >100 |
| 7c | 200 |
| 7d | >1000 |
| 7e | 340 |
| 7f | 570 |
| 8 | 38 |
| 9 | 190 |
| 10 | 9.6 |
| 10a | 53 |

TABLE 2

Enzyme Test PKC With Peptide Substrate
[Ser$^{25}$] PKC (19–31) and Myosin Light Chain Kinase

| Example | Inhibition of the Protein Kinases IC$_{50}$ (nM) | | Ratio of IC$_{50}$ MLC Kinase/ IC$_{50}$ C Kinase |
|---|---|---|---|
| | PKC | MLC Kinase | |
| 1  | 14  | 4600 | 328 |
| 1a | 6.3 | 1900 | 302 |
| 1b | 23  | 2400 | 104 |
| A  | 130 | 1300 | 10  |

A: 3-[1-(3-aminopropyl)-3-indolyl]-4-(1-methyl-3-indolyl)-1H-pyrrole-2,5-dione (EP 0328026)

The following examples are given for the purpose of illustrating the present invention:

EXAMPLE 1

2-[(1-Methyl)-1H-indol-3-yl]-3-(1-(3-L-serylaminopropyl)-1H-indol-3-yl)-maleinimide 2-[(1-methyl)-1H-indol-3-yl)-3-[1-(3-(N-FMOC-seryl)-aminopropyl)-1H-indol-3-yl]-maleinimide 100 mg (0.2 mmol) are dissolved in 5 mL dichloromethane, mixed with 1 mL piperidine, and stirred for 1 hour at ambient temperature. The solvent is distilled off in a vacuum and the residue is taken up in 10 mL diisopropyl ether and stirred up vigorously. The solid residue is separated off, again stirred up with diethyl ether, and 15 mg (21% of theory) of the desired product are isolated in the form of a solid red material;

mp 136°–140° C.;

RF=0.11 (dichloromethane/methanol—90:10%).

The 2-[(1-Methyl)-1H-indol-3-yl]-3-[1-[3-(N-FMOC-L-seryl)-aminopropyl]-1H-indol-3-yl]-maleinimide used as precursor is prepared in the following manner:

2-[(1-Methyl)-1H-indol-3-yl]-3-[1-[3-(N-FMOC-O-tert-butyl-L-seryl)-aminopropyl]-1H-indol-3-yl)-maleinimide 200 mg (0.2 mmol) in 1 mL dichloromethane are mixed at ambient temperature with 5 mL trifluoro-acetic acid and stirred for 3 hours. The reaction mixture is diluted with 50 mL dichloromethane, neutralized with a saturated solution of sodium hydrogen carbonate, and the organic phase is dried over anhydrous sodium sulphate. After distilling off the solvent in a vacuum, the residue is precipitated with diethyl ether. There are isolated 210 mg (100% of theory) of the desired product; mp 133°–135° C.; RF=0.39 (dichloromethane/methanol—90:10%).

The 2-[(1-methyl)-1H-indol-3-yl)-3-[1-[3-(N-FMOC-O-tert-butyl-L-seryl)-arninopropyl)-1H-indol-3-yl)-maleinimide used as starting material is prepared in the following manner:

2-[(1-Methyl)-1H-indol-3-yl]-3-[1-(3-aminopropyl)-1H-indol-3-yl)-maleinimide 100 mg (0.3 mmol), dissolved in 5 mL ethyl acetate, are mixed with 138 mg (0.3 mmol) N-FMOC-O-tert-butylserine pentafluorophenyl ester and 20 mg 1-hydroxy-1H-benzotriazole and stirred for 3 hours at ambient temperature. The reaction mixture is diluted with 50 mL ethyl acetate and the organic phase is washed with water, dried over anhydrous sodium sulphate, and the solvent distilled off in a vacuum. The residue is taken up in 10 mL ethyl acetate, a part of the product (120 mg) thereby precipitating out in pure form. The mother liquor is separated by column chromatography (silica gel, cyclohexane/ethyl acetate=50:50%), a further 60 mg of product being isolated (yield: 180 mg=94.2% of theory);

RF=0.71 (dichloromethane/methanol—90:10%).

The following compounds are obtained in a manner analogous to that described in Example 1:

1a) 2-[(1-Methyl)-1H-indol-3-yl]-3-[1-(3-β-alanylaminopropyl)-1H-indol-3-yl]-maleinimide;

mp 95°–103° C.;

RF=0.12 (dichloromethane/methanol—90:10%);

1b) 2-[(1-Methyl)-1H-indol-3-yl]-3-[1-(3-β-alanylaminopropyl)-1H-indol-3-yl]-maleinimide;

mp 118°–127° C.;

RF=0.19 (chloroform/methanol/concentrated solution of ammonia=250:50:8).

EXAMPLE 2

2-[(1-Methyl)-1H-indol-3-yl)-3-[1-(3-D-alanylaminopropyl)-1H-indol-3-yl]-maleinimide 2-[(1-Methyl)-1H-indol-3-yl)-3-[1-(3-N-BOC-D-alanylaminopropyl)-1H-indol-3-yl)-maleinimide 115 mg (0.2 mmol) are dissolved in 5 mL dichloromethane, mixed with 3 mL trifluoroacetic acid, and stirred for 6 hours at ambient temperature. The reaction solution is diluted with 50 mL dichloromethane, neutralized with a solution of sodium hydrogen carbonate, and dried over anhydrous sodium sulphate. After distilling off the solvent in a vacuum, the residue is separated on preparative thick layer plates (silica gel, dichloromethane/methanol saturated with ammonia=90:10%).

The 2-[(1-methyl)-1H-indol-3-yl)-3-[1-(3-N-BOC-D-alanylaminopropyl)-1H-indol-3-yl]-maleinimide used as precursor is prepared in the following way:

2-[(1-Methyl)-1H-indol-3-yl]-3-[1-(3-aminopropyl)-1H-indol-3-yl)-maleinimide 80 mg (0.2 mmol) are dissolved in 2 mL ethyl acetate and 1 mL dimethylformamide and mixed with 58 mg (0.2 mmol) N-BOC-D-alanine-O-succinimidyl ester. The reaction mixture is stirred for 18 hours at ambient temperature and diluted with 50 mL ethyl acetate. The organic phase is washed twice with water, dried over anhydrous sodium sulphate, and the solvent distilled off therefrom in a vacuum. The residue (115 mg) is used for the next step without further purification.

The following compounds are obtained in a manner analogous to that described in Example 2:

2a) 2-[(1-Methyl)-1H-indol-3-yl]-3-[1-(4-L-alanylaminobutylyl)-1H-indol-3-yl)-maleinimide;

mp 90°–102° C.;

RF=0.15 (dichloromethane/methanol saturated with ammonia=90:10%).

2b) 2-[(1-Methyl)-1H-indol-3-yl]-3-[1-(4-L-arginylaminobutyl)-1H-indol-3-yl]-maleinimide;

mp 158°–172° C.;

RF=0.42 (chloroform/methanol/concentrated ammonia solution=250:50:8).

2c) 2-[(1-Methyl)-1H-indol-3-yl]-3-[1-(5-L-alanylaminopentyl)-1H-indol-3-yl]-maleinimide;

mp 96°–1060° C.;

RF=0.12 (dichloromethane/methanol—90:10%).

2d) 2-[(1-Methyl)-1H-indol-3-yl]-3-[1-(9-L-alanylaminononyl)-1H-indol-3-yl)-maleinimide;

mp 90°–95° C.;

RF=0.12 (dichloromethane/methanol-90:10%).

2e) 2-[(1-Methyl)-1H-indol-3-yl]-3-[1-(9-L-serylaminononyl)-1H-indol-3-yl]-maleinimide;

mp 95°–97° C.;

RF=0.24 (dichloromethane/methanol=90:10%).

2f) 2-[(1-Methyl)-1H-indol-3-yl]-3-[1-(9-L-alanylaminooctyl)-1H-indol-3-yl)-maleinimide;

mp 80°–91° C.;

RF=0.16 (dichloromethane/methanol—90:10%).

2g) 2-[(1-Methyl)-1H-indol-3-yl]-3-[1-(9-L-serylaminooctyl)-1H-indol-3-yl]-maleinimide;

mp 86°–94° C.;

RF=0.72 (chloroform/methanol/concentrated ammonia solution=250:50:8).

EXAMPLE 3

2-[(1-Methyl)-1H-indol-3-yl]-3-[1-[3-(5-L-serylaminopentanoyl)-aminopropyl)-1H-indol-3-yl)-maleinimide 2-[(1-Methyl)-1H-indol-3-yl)-3-[1-[3-[5-(N-FMOC-L-seryl)-aminopentanoyl)-aminopropyl)-1H-indol-3-yl)-maleinimide 40 mg (0.05 mol) are dissolved in 4 mL anhydrous tetrahydrofuran, mixed with 40 mg (0.5 mmol) diethylamine, and stirred for 18 hours at ambient temperature. Subsequently, the solvent is distilled off in a vacuum and the residue separated by thick layer chromatography (silica gel, dichloromethane/ methanol saturated with ammonia=90:10%). The fraction with an RF value of 0.52 is isolated and the product is extracted. After distilling off the solvent in a vacuum, there are isolated 15 mg (51% of theory) of the desired product;

mp 145°–175° C.

The 2-[(1-methyl)-1H-indol-3-yl)-3-[1-[3-[5-(N-FMOC-L-seryl)-aminopentanoyl]-aminopropyl)-1H-indol-3-yl)-maleinimide used as precursor is prepared in the following manner:

2-[(1-Methyl)-1H-indol-3-yl]-3-[1-[3-[5-(N-FMOC-O-tertbutyl-L-seryl)-aminopentanoyl]-aminopropyl]-1H-indol-3-yl]-maleinimide 13 mg (0.015 mmol) are dissolved in 1 mL dichloromethane and reacted in the presence of 4 mL trifluoroacetic acid within the course of 2 days. The reaction mixture is diluted with 50 mL dichloromethane, neutralized with an aqueous solution of sodium hydrogen carbonate, and the organic phase dried over anhydrous sodium sulphate. After distilling off the solvent in a vacuum, the residue is stirred with diethyl ether/n-pentane, filtered off with suction, and dried. There are obtained 10 mg (83% of theory) of the desired product.

The 2-[(1-methyl)-1H-indol-3-yl)-3-[1-[3-[5-(N-FMOC-O-tert-butyl-L-seryl)-aminopentanoyl]-aminopropyl)-1H-indol-3-yl)-maleinimide used as precursor is prepared analogously to Example 1 from 2-[(1-methyl)-1H-indol-3-yl]-3-[1-[3-(4-aminopentanoyl)-aminopropyl)-1H-indol-3-yl)-maleinimide; yield 29% of theory.

The 2-[(1-methyl)-1H-indol-3-yl]-3-[1-[3-(4-aminopentanoyl)-aminopropyl)-1H-indol-3-yl)-maleinimide used as precursor is obtained from 2-[(1-methyl)-1H-indol-3-yl]-3-[1-[3-(4N-FMOC-aminopentanoyl)-aminopropyl]-1H-indol-3-yl)-maleinimide by splitting off the FMOC group analogously to Example 1;

yield 69% of theory.

The 2-[(1-methyl)-1H-indol-3-yl)-3-[1-[3-(4N-FMOC-aminopentanoyl)-aminopropyl]-1H-indol-3-yl]-maleinimide used as precursor is obtained by the reaction of 2-[(1-methyl)-1H-indol-3-yl]-3-[1-(3-aminopropyl)-1H-indol-3-yl]-maleinimide with 5N-FMOC-aminovaleric acid pentafluorophenyl ester analogously to Example 1;

RF=0.54 (dichloromethane/methanol saturated with ammonia=90:10%).

EXAMPLE 4

2-[(1-Methyl)-1H-indol-3-yl)-3-[1-[3-(L-alanylglycyl)-aminopropyl]-1H-indol-3-yl]

2-[(1-Methyl)-1H-indol-3-yl]-3-[1-[3-(N-BOC-L-alanylseryl)-aminopropyl)-1H-indol-3-yl)-maleinimide 95 mg (0.15 mmol) are dissolved in 4 mL dichloromethane and, after the addition of 175 mg trifluoroacetic acid, stirred for 24 hours at ambient temperature. The reaction mixture is diluted with 50 mL dichloromethane and neutralized with an aqueous solution of sodium hydrogen carbonate. The organic phase is dried over anhydrous sodium sulphate and the solvent is distilled off in a vacuum. The residue is separated by thick layer chromatography (silica gel, dichloromethane/ methanol saturated with ammonia=90:10%). The fraction with the RF of 0.37 is isolated, the crude product is extracted therefrom and, after distilling off the solvent in a vacuum, there are obtained 16 mg (20% of theory) of the desired product;

mp 126°–138° C.

The 2-[(1-methyl)-1H-indol-3-yl)-3-[1-[3-(N-BOC-L-alanylseryl)-aminopropyl)-1H-indol-3-yl)-maleinimide used as precursor is obtained in the following manner:

2-[(1-Methyl)-1H-indol-3-yl)-3-[1-(3-aminopropyl)-1H-indol-3-yl)-maleinimide, 185 mg (0.5 mmol) N-BOC-alanylglycine and 155 mg (0.75 mmol) dicyclohexylcarbodiimide are successively dissolved in a solvent comprising 3 mL anhydrous tetrahydrofuran and 2 mL dimethylformamide and reacted with one another for 6 hours at ambient temperature. The reaction mixture is poured into 300 mL of water, the organic components are extracted with dichloromethane, and the organic phase is washed with water and dried over anhydrous sodium sulphate. After distilling off the solvent in a vacuum, the residue is separated by thick layer chromatography (silica gel, dichloromethane/ methanol—90:10%). The fraction with an RF value of 0.41 is separated, the product is extracted and, after distilling off the solvent in a vacuum, is isolated in the form of a red resin.

In a manner analogous to that described in Example 4, the following compound is prepared:

4a) 2-[(1-Methyl)-1H-indol-3-yl]-3-[1-[3-(L-alanyl-β-alanyl)-aminopropyl]-1H-indol-3-yl)-maleinimide;

mp 103°–112° C.;

RF=0.36 (chloroform/methanol/concentrated ammonia solution=250:50:8).

EXAMPLE 5

3-[3-[4-(1-Methylindol-3-yl)-1H-pyrrole-2,5-dion-3-yl]-indol-1-yl)-propionyl-L-alanine 3-[3-[4-(1-Methylindol-3-yl)-1H-pyrrole-2,5-dion-3-yl)-indol-1-yl]-propionyl-L-alanine methyl ester 100 mg (0.2 mmol) are dissolved in a mixture of 4 mL dioxane and 1 mL of water, mixed with 36 mg (1.5 mmol) lithium hydroxide, and stirred for 18 hours at ambient temperature. The solvent is subsequently distilled off in a vacuum and the residue is taken up in 30 mL ethylacetate, washed with 1N hydrochloric acid, and dried over anhydrous sodium sulphate. The solvent is then distilled off in a vacuum and the residue separated by thick layer chromatography (silica gel, dichloromethane/methanol saturated with ammonia=90:10%). The product is separated with the first polar fraction, extracted, freed from solvent, and stirred up with a mixture of dichloromethane and diisopropyl ether (1:1). There are obtained 65 mg (67% of theory) of the desired product;

mp 240°–255° C.;

RF=0.06 (chloroform/methanol/concentrated ammonia solution=250:50:8).

EXAMPLE 6
3-[3-[4-(1-Methylindol-3-yl)-1H-pyrrole-2,5-dion-3-yl)-indol-1-yl)-propionyl-L-alanine methyl ester 3-[3-[4-(1-Methylindol-3-yl)-1H-pyrrole-2,5-dion-3-yl]-indol-1-yl)-propionic acid 272 mg (0.65 mmol) are dissolved in 3 mL anhydrous tetrahydrofuran and mixed with 145 mg (0.70 mmol) dicyclohexylcarbodiimide and a mixture of 90 mg (0.8 mmol) alanine ethyl ester hydrochloride and 85 mg triethylamine dissolved in 5 mL anhydrous tetrahydrofuran. The reaction mixture is stirred for 24 hours at ambient temperature, the solvent is then distilled off in a vacuum, the residue is taken up in 100 mL ethyl acetate, and the organic phase is washed with water. After drying over anhydrous sodium sulphate and distilling off the solvent in a vacuum, the crude product obtained is separated by thick layer chromatography (silica gel, dichloromethane/methanol=90:10%). The fraction with the RF of 0.31 is separated, the product is extracted and, after removal of the solvent in a vacuum, there are isolated 130 mg (40% of theory) of the desired product;

mp 142°–149° C.

The 3-[3-[4-(1-methylindol-3-yl)-1H-pyrrole-2,5-dion-3-yl]-indol-1-yl)-propionic acid used as precursor is prepared in the following manner:

3-[3-[4-(1-Methylindol-3-yl)-furane-2,5-dion-3-yl)-propionic acid 210 mg (0.5 mmol) are dissolved in 2 mL dimethylformamide, mixed with 4 mL of a concentrated solution of ammonium hydroxide and heated to the boil for 6 hours. The reaction mixture is allowed to cool, poured into 200 mL of water, and the product is obtained by extraction with ethyl acetate. The organic phase is washed twice with water, dried over anhydrous sodium sulphate, and freed from solvent in a vacuum. The product is isolated in a yield of 82% of theory;

mp 244°–253° C.

The 3-[3-[4-(1-methylindol-3-yl)-furane-2,5-dion-3-yl]-indol-1-yl]-propionic acid used as precursor is prepared in the following manner:

2-[(1-Methyl)-1H-indol-3-yl)-3-[1-(2-cyanoethyl)-1H-indol-3-yl]-maleinimide 0.5 g (1.2 mmol) is heated under reflux for 3 hours in a 10% solution of potassium hydroxide in water. The cooled reaction solution is acidified with acetic acid, the red precipitate obtained is filtered off with suction, washed neutral, and stirred in a mixture of methanol and water. After drying, there is isolated 0.4 g (80% of theory) of the desired product in the form of an ochre-colored powder.

The following syntheses were carried out on solid phases with the RAMPS® synthesis apparatus using, as solid phase material, RAPIDAMIDE resin of the firm DuPont.

EXAMPLE 7
3-[3-[4-(1-Methylindol-3-yl)-1H-pyrrole-2,5-dion-3-yl]-indol-1-yl)-propionyl-L-alanylglycyl-L-lysinamide Resin (0.1 mmol) is activated according to the instructions and reacted over the course of 1 hour with 0.4 mmol FMOC-L-arginine(Pmc)-OPfp in 2.5 mL acetic acid dimethylamide in the presence of 1-hydroxy-1H-benzotriazole. Excess reagents are washed out, the FMOC protective group is removed with piperidine, and the resin again washed with acetic acid dimethylamide. Subsequently and in the same manner, there are successively condensed on glycine, L-alanine, and 2-[(1-methyl)-1H-indol-3-yl]-3-[1-(2-hydroxycarbonyleth yl)-1H-indol-3-yl]-maleinimide. The product is thereafter split off by treating the resin over the course of 18 hours with a mixture of 300 mg phenol in 2 mL trifluoroacetic acid. The dark red reaction solution is filtered off from the solid materials, freed from solvent in a vacuum, and the crude product is precipitated out by treatment with diethyl ether. The solid precipitate is filtered off with suction, subsequently stirred with ethyl acetate, again filtered off with suction, and subsequently washed with diethyl ether. There are isolated 15 mg of the desired product;

mp 158°–160° C.;

RF=0.55 (butanol/pyridine/acetic acid/water= 30:20:6:24).

The following compounds are prepared by methods analogous to Example 7:

7a) 3-[3-[4-(1-methylindol-3-yl)-1H-pyrrole-2,5-dion-3-yl]-indol-1-yl)-propionyl-L-lysyl-L-asparaginyl-L-arginyl-L-phenylalanyl-L-alaninamide;

mp 193°–195° C.;

RF=0.48 (butanol/pyridine/acetic acid/water= 30:20:6:24).

7b) 3-[3-[4-(1-methylindol-3-yl)-1H-pyrrole-2,5-dion-3-yl]-indol-1-yl)-propionylglycylglycyl-L-alaninamide;

mp 125°–130° C.;

RF=0.74 (propan-2-ol/acetic acid/water=4:1:1).

7c) 3-[3-[4-(1-methylindol-3-yl)-1H-pyrrole-3,5-dion-3-yl]-indol-1-yl]-propionylglycylglycyl-L-serylamide;

mp 142°–146° C.;

RF=0.71 (propan-2-ol/acetic acid/water=4:1:1).

7d) 3-[3-[4-(1-methylindol-3-yl)-1H-pyrrole-2,5-dion-3-yl)-indol-1-yl)-propionyl-L-serylglycyl-L-alaninamide;

mp 165°–167° C.;

RF=0.73 (propan-2-ol/acetic acid/water=4:1:1).

7e) 3-[3-[4-(1-methylindol-3-yl)-1H-pyrrole-2,5-dion-3-yl)-indol-1-yl)-propionylglycylglycylglycyl-L-alanylamide;

mp 157°–159° C.;

RF=0.65 (propan-2-ol/acetic acid/water=4:1:1).

7f) 3-[3-[4-(1-methylindol-3-yl)-1H-pyrrole-2,5-dion-3-yl)-indol-1-yl]-propionyl-L-lysylglycyl-L-alanylamide;

mp 146°–148° C.;

RF=0.47 (propan-2-ol/acetic acid/water=4:1:1).

EXAMPLE 8
12-[2-(3-L-Alanyl)-aminopropyl)-6,7,12,13-tetrahydro-13-methyl-5,7-dioxo-5H-indolo[2,3-a]pyrrolo[3,4-c]-carbazole 12-[2-(N-BOC-L-alanyl)-amino-propyl]-6,7,12,13-tetrahydro-13-methyl-5,7-dioxo-5H-indolo[2,3-a]pyrrolo-[3,4-c]carbazole 50 mg (0.1 mmol) are dissolved in 5 mL dichloromethane at ambient temperature and mixed with 3 mL trifluoroacetic acid. The reaction mixture is stirred for 3 hours at this temperature, diluted with 50 mL dichloromethane, neutralized with an aqueous solution of sodium hydrogen carbonate, the organic phase is dried over anhydrous sodium sulphate, the solvent is distilled off in a vacuum, and the residue is recrystallized from ethanol. After leaving to stand at −20° C. there are obtained 15 mg (37% of theory) of the desired product;

mp 141°–144° C.;

RF=0.29 (dichloromethane/methanol=90:10%).

The 12-[2-(N-BOC-L-alanyl)-aminopropyl)-6,7,12,13-tetrahydro-13-methyl-5,7-dioxo-5H-indolo[2,3-pyrrolo-[3,4-c]carbazole used as precursor is synthesized in the following manner:

12-[2-(3-Aminopropyl)-6,7,12,13-tetrahydro-13-methyl-5,7-dioxo-5H-indolo[2,3-a]pyrrolo-[3,4-c]-carbazole 34 mg (0.1 mmol) are combined, while stirring at ambient temperature, with 25 mg (0.1 mmol) N-BOC-L-alanine-N-hydroxysuccinimidyl ester in 3 mL ethyl acetate and 1 mL dimethylformamide and stirred for 3 hours. The reaction solution is then diluted with 50 mL ethyl acetate and washed twice with water. After drying the organic phase over anhydrous sodium sulphate, the solvent is distilled off in a vacuum, and the crude product is used without further purification for the next step;

RF=0.62 (dichloromethane/methanol—90:10%).

The 12-[2-(3-aminopropyl)-6,7,12,13-tetrahydro-13-methyl-5,7-dioxo-5H-indolo[2,3-a]pyrrolo[3,4-c]-carbazole used as precursor is prepared in the following manner:

12-(2-Cyanoethyl)-6,7,12,13-tetrahydro-13-methyl-5,7-dioxo-5H-indolo[2,3-a)pyrrolo-[3,4-c]carbazole 200 mg (0.5 mmol) are hydrogenated in the presence of 250 mg Raney nickel (BK 111 W (Mo doped) in 25 mL of a solvent mixture of methanol saturated with ammonia/tetrahydrofuran (2:2) with hydrogen at a pressure of 50 to 60 bar and at a temperature of 60° C. for 48 hours. The reaction mixture is subsequently filtered, the residue is then washed three times with, in each case, 10 mL of methanol, the filtrate is freed from solvent in a vacuum, and the residue is precipitated from ethyl acetate. There are isolated 100 mg (49% of theory) of the desired product;

RF=0.16 (dichloromethane/methanol=90:10%).

The 12-(2-cyanoethyl)-6,7,12,13-tetrahydro-13-methyl-5,7-dioxo-5H-indolo[2,3-a]pyrrolo[3,4-c]-carbazole used as precursor is prepared in the following manner:

A reaction mixture of 4.6 g (11.7 mmol) 2-[(1-methyl)-1H-indol-3-yl]-3-[1-(cyanoethyl)-1H-indol-3-yl)-maleinimide, 4.4 g (23.3 mmol) p-toluene-sulphonic acid hydrate and 3.8 g (16.7 mmol) DDQ in 600 mL toluene is heated under reflux for 2.5 hours. The solvent is distilled off in a vacuum and the residue is separated by column chromatography (basic aluminium oxide, acetone/ethanol—95:5%). With the second fraction there are isolated 500 mg (11% of theory) of the desired product in the form of a yellow powder;

RF=0.69 (dichloromethane/methanol—90:10%).

EXAMPLE 9

12-[2-(L-Alanyl-L-arginyl)-aminopropyl]-6,7,12,13-tetrahydro-13-methyl-5,7-dioxo-5H-indolo[2,3-a]pyrrolo-[3,4-c]carbazole The synthesis takes place analogously to Example 4. However, as precursors there are used 12-[2-(3-aminopropyl))-6,7,12,13-tetrahydro-13-methyl-5,7-dioxo-5H-indolo[2,3-a]pyrrolo[3,4-c]carbazole and BOC-L-arginyl-(Z2)-BOC-L-alanine;

mp 164°–166° C.;

RF=0.04 (chloroform/methanol/concentrated solution of ammonia=250:50:8).

EXAMPLE 10

12-[2-(4-L-Alanyl)-aminobutyl]-6,7,12,13-tetrahydro-13-methyl-5,7-dioxo-5H-indolo[2,3-a]pyrrolo[3,4-c]-carbazole The synthesis is carried out analogously to Example 9;

mp 122°–126° C.;

RF=0.17 (dichloromethane/methanol—90:10%).

The 12-[2-(4-aminobutyl)]-6,7,12,13-tetrahydro-13-methyl-5,7-dioxo-5H-indolo[2,3-a]pyrrolo[3,4-c]-carbazole used as precursor is prepared in the following manner:

12-[2-(4-Azidobutyl))-6,7,12,13-tetrahydro-13-methyl-5,7-dioxo-5H-indolo[2,3-a]pyrrolo-[3,4-c]-carbazole 300 mg (0.7 mmol) are hydrogenated in 40 mL of a solvent mixture of tetrahydrofuran/ethanol (1:1) in the presence of 300 mg palladium on charcoal (5%, anhydrous) at a pressure of 50 bar and at a temperature of 25° C. with hydrogen over the course of 24 hours. The reaction mixture is then filtered, the solvent is distilled off in a vacuum, and the residue is stirred from ethanol. There are isolated 250 mg (89% of theory) of the desired product;

RF=0.18 (chloroform/methanol/concentrated ammonia solution=250:50:8).

The 12-[2-(4-azidobutyl))-6,7,12,13-tetrahydro-13-methyl-5,7-dioxo-5H-indolo[2,3-a]pyrrolo[3,4-c]-carbazole used as precursor is prepared in the following manner:

A reaction mixture of 1.6 g (3.7 mmol) 2-[(1-methyl)-1H-indol-3-yl]-3-[1-(4-azidobutyl)-1H-indol-3-yl]-maleinimide, 1.4 g (7.4 mmol) p-toluenesulphonic acid hydrate and 1.25 g (5.5 mmol) DDQ in 500 mL toluene is heated under reflux for 30 minutes. The solvent is distilled off in a vacuum and the residue is separated by column chromatography (basic aluminium oxide, acetone/ethanol=95:5%). With the second fraction there are isolated 356 mg (22% of theory) of the desired product in the form of a bright yellow powder;

RF=0.88 (dichloromethane/methanol=90:10%).

In a manner analogous to that described in Example 10, the following compound is prepared:

10a) 12-[2-(5-L-alanyl)-aminopentyl]-6,7,12,13-tetrahydro-13-methyl-5,7-dioxo-5H-indolo[2,3-a]pyrrolo-[3,4-c]carbazole;

mp 160°–163° C.;

RF=0.27 (dichloromethane/methanol—90:10%).

Table 3 below lists some compounds of the invention. The list is not intended to be a limitation of the scope of the invention.

TABLE 3

| Example | A | $R^1$ | X | Y | $E_n$-$R^5$ |
|---|---|---|---|---|---|
| 1 | bisindole | $CH_3$ | $(CH_2)_3$ | NH | Ser |
| 1a | bisindole | $CH_3$ | $(CH_2)_3$ | NH | Ala |
| 1b | bisindole | $CH_3$ | $(CH_2)_3$ | NH | bAla |
| 2 | bisindole | $CH_3$ | $(CH_2)_3$ | NH | DAla |
| 2a | bisindole | $CH_3$ | $(CH_2)_4$ | NH | Ala |
| 2b | bisindole | $CH_3$ | $(CH_2)_4$ | NH | Arg |
| 2c | bisindole | $CH_3$ | $(CH_2)_5$ | NH | Ala |
| 2d | bisindole | $CH_3$ | $(CH_2)_9$ | NH | Ala |
| 2e | bisindole | $CH_3$ | $(CH_2)_9$ | NH | Ser |
| 2f | bisindole | $CH_3$ | $(CH_2)_8$ | NH | Ala |

TABLE 3-continued

| Example | A | R¹ | X | Y | E$_n$-R$^5$ |
|---|---|---|---|---|---|
| 2g | bisindole | CH$_3$ | (CH$_2$)$_8$ | NH | Ser |
| 3 | bisindole | CH$_3$ | (CH$_2$)$_3$ | NH | 4Ava—Ser |
| 4 | bisindole | CH$_3$ | (CH$_2$)$_3$ | NH | Gly—Ala |
| 4a | bisindole | CH$_3$ | (CH$_2$)$_3$ | NH | bAla—Ala |
| 5 | bisindole | CH$_3$ | (CH$_2$)$_2$ | CO | Ala—OH |
| 6 | bisindole | CH$_3$ | (CH$_2$)$_2$ | CO | Ala—O—CH$_3$ |
| 7 | bisindole | CH$_3$ | (CH$_2$)$_2$ | CO | Ala—Gly—Lys—NH$_2$ |
| 7a | bisindole | CH$_3$ | (CH$_2$)$_2$ | CO | Lys—Asp—Arg—Phe—Ala—NH$_2$ |
| 7b | bisindole | CH$_3$ | (CH$_2$)$_2$ | CO | Gly—Gly—Ala—NH$_2$ |
| 7c | bisindole | CH$_3$ | (CH$_2$)$_2$ | CO | Gly—Gly—Ser—NH$_2$ |
| 7d | bisindole | CH$_3$ | (CH$_2$)$_2$ | CO | Ser—Gly—Ala—NH$_2$ |
| 7e | bisindole | CH$_3$ | (CH$_2$)$_2$ | CO | Gly—Gly—Gly—Ala—NH$_2$ |
| 7f | bisindole | CH$_3$ | (CH$_2$)$_2$ | CO | Lys—Gly—Ala—NH$_2$ |
| 8 | carbazole | CH$_3$ | (CH$_2$)$_3$ | NH | Ala |
| 9 | carbazole | CH$_3$ | (CH$_2$)$_3$ | NH | Ala—Arg |
| 10 | carbazole | CH$_3$ | (CH$_2$)$_4$ | NH | Ala |
| 10a | carbazole | CH$_3$ | (CH$_2$)$_5$ | NH | Ala |

We claim:
1. A compound of formula

in which A is a radical of formula (III)

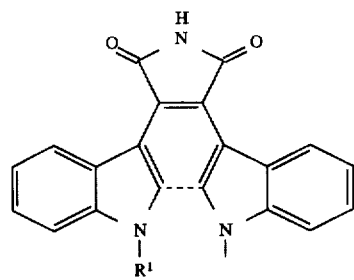

Formula III wherein R$^1$ is a hydrogen atom or an alkyl radical containing 1 to 4 carbon atoms and (---) is open or is a valency bond, such that A is bis-indolylmaleinimide or indolopyrrolocarbazole of Formula III, X is a single bond or an alkylene radical containing up to 16 carbon atoms, Y is a single bond or a group such as N—R$^2$, CO, CS, CH=CH, PO (OH)O, SO$_2$, wherein R$^2$ is a hydrogen atom or an alkyl radical containing 1 to 4 carbon atoms, n is 1 to 20, E are either the same or different radicals of the formula IV:

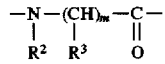

or of the Formula V:

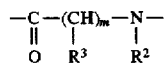

in which, when m is 1, R$^3$ is either a hydrogen atom or the side group of one of the natural α-aminocarboxylic acids and, when m is 2 to 6, R$^3$ is a hydrogen atoms, and when E is a radical of Formula IV, R$^5$ is an amino group or the radical —OR$^4$, in which R$^4$ is an alkyl radical containing 1 to 4 carbon atoms or a hydrogen atom, and when E is a radical of formula V, R$^5$ is a hydrogen atom; or the pharmacologically compatible salts thereof.

2. A compound according to claim 1, wherein

R$^1$ is methyl;

X is methylene, propylene, butylene, pentylene, octylene, or nonylene;

Y is NH or CO; and

—E$_n$—R$^5$ is alanine, alanine methyl ester, β-alanine, arginine, serine, glycylalanine, glycylglycylalanine, glycylglycylglycylalanine, glycylglycylserine, lysylglycylalanine, seryl-glycylalanine, alanylglycyllysine, lysylasparaginylarginylphenylalanylalanine, β-alanylalanine, 4-aminovalerianoylserine, or alanylarginine.

3. A compound according to claim 1, selected from the group consisting of:

2-[(1-methyl)-1H-indol-3-yl)-3-[1-(3-L-serylaminopropyl)-1H-indol-3-yl]-maleinimide;

2-[(1-methyl)-1H-indol-3-yl)-3-[1-(3-L-alanylaminopropyl)-1H-indol-3-yl]-maleinimide;

2-[(1-methyl)-1H-indol-3-yl)-3-[1-(3-β-alanylaminopropyl)-1H-indol-3-yl)-maleinimide;

2-[(1-methyl)-1H-indol-3-yl)-3-[1-(3-D-alanylaminopropyl)-1H-indol-3-yl)-maleinimide;

2-[(1-methyl)-1H-indol-3-yl)-3-[1-(4-L-alanylaminobutylyl)-1H-indol-3-yl]-maleinimide;

2-[(1-methyl)-1H-indol-3-yl)-3-[1-(4-L-arginylaminobutyl)-1H-indol-3-yl]-maleinimide;

2-[1-methyl)-1H-indol-3-yl]-3-[1-(5-L-alanylaminopentyl)-1H-indol-3-yl]-maleinimide;

2-[(1-methyl)-1H-indol-3-yl)-3-[1-(9-L-alanylaminononyl)-1H-indol-3-yl)-maleinimide;

2-[(1-methyl)-1H-indol-3-yl)-3-[1-(9-L-serylaminononyl)-1H-indol-3-yl]-maleinimide;

2-[(1-methyl)-1H-indol-3-yl)-3-[1-(9-L-alanylaminooctyl)-1H-indol-3-yl)-maleinimide;

2-[(1-methyl)-1H-indol-3-yl]-3-[1-(9-L-serylaminooctyl)-1H-indol-3-yl]-maleinimide;

2-[(1-methyl)-1H-indol-3-yl]-3-[1-[3-(5-L-serylaminopentanoyl)-aminopropyl)-1H-indol-3-yl)-maleinimide;

2-[(1-methyl)-1H-indol-3-yl]-3-[1-[3-(L-alanylglycyl)-aminopropyl]-1H-indol-3-yl]-maleinimide;

2-[(1-methyl)-1H-indol-3-yl]-3-[1-[3-(L-alanyl-β-alanyl)-aminopropyl]-1H-indol-3-yl]-maleinimide;

3-[3-[4-(1-methylindol-3-yl)-1H-pyrrole-2,5-dion-3-yl]-indol-1-yl)-propionyl-L-alanine;

3-[3-[4-(1-methylindol-3-yl)-1H-pyrrole-2,5-dion-3-yl]-indol-1-yl]-propionyl-L-alanine methyl ester;

3-[3-[4-(1-methylindol-3-yl)-1H-pyrrole-2,5-dion-3-yl]-indol-1-yl]-propionyl-L-alanylglycyl-L-lysinamide;

3-[3-[4-(1-methylindol-3-yl)-1H-pyrrole-2,5-dion-3-yl]-indol-1-yl]-propionyl-L-lysyl-L-asparaginyl-L-arginyl-L-phenylalanyl-L-alaninamide;

3-[3-[4-(1-methylindol-3-yl)-1H-pyrrole-2,5-dion-3-yl]-indol-1-yl]-propionylglycylglycyl-L-alaninamide;

3-[3-[4-(1-methylindol-3-yl)-1H-pyrrole-2,5-dion-3-yl]-indol-1-yl]-propionylglycylglycyl-L-serylamide;

3-[3-[4-(1-methylindol-3-yl)-1H-pyrrole-2,5-dion-3-yl]-indol-1-yl)-propionyl-L-serylglycyl-L-alaninamide;

3-[3-[4-(1-methylindol-3-yl)-1H-pyrrole-2,5-dion-3-yl]-indol-1-yl]-propionylglycylglycyl-glycyl-L-alanylamide;

3-[3-[4-(1-methylindol-3-yl)-1H-pyrrole-2,5-dion-3-yl)-indol-1-yl]-propionyl-L-lysylglycyl-L-alanylamide;

12-[2-(3-L-alanyl)-aminopropyl)-6,7,12,13-tetrahydro-13-methyl-5,7-dioxo-5H-indolo[2,3-a]pyrrolo[3,4-c]carbazole;

12-[2-(L-alanyl-L-arginyl)-aminopropyl)-6,7,12,13-tetrahydro-13-methyl-5,7-dioxo-5H-indolo[2,3-a]pyrrolo[3,4-c]carbazole;

12-[2-(4-L-alanyl)-aminobutyl)-6,7,12,13-tetrahydro-13-methyl-5,7-dioxo-5H-indolo[2,3-a]pyrrolo[3,4-c]carbazole; and 12-[2-(5-L-alanyl)-aminopentyl]-6,7,12,13-tetrahydro-13-methyl-5,7-dioxo-5H-indolo[2,3-a]pyrrolo[3,4-c]carbazole.

4. A pharmaceutical composition comprising a therapeutically effective amount of a compound according to claim 1 together with a pharmaceutically acceptable carrier.

5. A method of inhibiting protein kinase C which comprises administering to a patient in need of such treatment a compound according to claim 1 in unit dosage form.

6. A method of treating heart and blood vessel diseases which comprises administering to a patient in need of said treatment a compound according to claim 1 in unit dosage form.

7. A method of treating cancer which comprises administering to a patient in need of said treatment a compound according to claim 1 in unit dosage form.

8. A method of treating viral diseases which comprises administering to a patient in need of said treatment a compound according to claim 1 in unit dosage form.

9. A method of treating thrombosis which comprises administering to a patient in need of said treatment a compound according to claim 1 in unit dosage form.

10. A method of treating heart rhythm disturbances which comprises administering to a patient in need of said treatment a compound according to claim 1 in unit dosage form.

11. A method of treating atherosclerosis which comprises administering to a patient in need of said treatment a compound according to claim 1 in unit dosage form.

12. A method of treating bronchopulmonary diseases which comprises administering to a patient in need of said treatment a compound according to claim 1 in unit dosage form.

13. A method of treating degenerative diseases of the central nervous system which comprises administering to a patient in need of said treatment a compound according to claim 1 in unit dosage form.

14. A method of treating inflammatory diseases which comprises administering to a patient in need of said treatment a compound according to claim 1 in unit dosage form.

15. A method of treating diseases of the immune system which comprises administering to a patient in need of said treatment a compound according to claim 1 in unit dosage form.

16. A method of treating psoriasis which comprises administering to a patient in need of said treatment a compound according to claim 1 in unit dosage form.

17. A method of suppressing an immune system which comprises administering to a patient in need of said treatment a compound according to claim 1 in unit dosage form.

* * * * *